(12) United States Patent
Nagarkar et al.

(10) Patent No.: US 9,995,600 B2
(45) Date of Patent: Jun. 12, 2018

(54) MULTI-AXIS MAGNETO-RESISTANCE SENSOR PACKAGE

(71) Applicant: General Electric Company, Schenectady, NY (US)

(72) Inventors: Kaustubh Ravindra Nagarkar, Clifton Park, NY (US); Peter William Lorraine, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 14 days.

(21) Appl. No.: 14/842,578

(22) Filed: Sep. 1, 2015

(65) Prior Publication Data
US 2017/0059361 A1    Mar. 2, 2017

(51) Int. Cl.
*G01R 33/06* (2006.01)
*G01D 5/16* (2006.01)
(Continued)

(52) U.S. Cl.
CPC .......... *G01D 5/16* (2013.01); *G01R 33/0005* (2013.01); *G01R 33/0017* (2013.01); *G01R 33/0052* (2013.01); *G01R 33/0206* (2013.01)

(58) Field of Classification Search
CPC ......... G06F 2221/2129; G06F 12/0866; G06F 1/1626; G06F 9/226; G06F 9/3885;
(Continued)

(56) References Cited

U.S. PATENT DOCUMENTS

| 5,689,185 A | 11/1997 | Widdershoven et al. |
| 5,850,624 A | 12/1998 | Gard et al. |

(Continued)

FOREIGN PATENT DOCUMENTS

| DE | 102005023591 A1 | 11/2006 |
| WO | 2014059110 A1 | 4/2014 |

OTHER PUBLICATIONS

European Search Report and Opinion issued in connection with corresponding EP Application No. 16184430.3 dated Jan. 30, 2017.
Popovic et al., "Multi-Axis Integrated Hall Magnetic Sensors," Nuclear Technology & Radiation Protection, vol. 22, No. 1, 2007, pp. 20-28.

*Primary Examiner* — Vinh Nguyen
(74) *Attorney, Agent, or Firm* — Ziolkowski Patent Solutions Group, SC; Jean K. Testa

(57) ABSTRACT

A system and method for providing a position and orientation sensor package having a reduced size in at least one dimension is disclosed. The position and orientation sensor package includes a dielectric substrate and a first magneto-resistance sensor chip attached to the dielectric substrate, the first magneto-resistance sensor chip including at least one magneto-resistance sensor circuit. The position and orientation sensor package also includes a second magneto-resistance sensor chip attached to the dielectric substrate and positioned adjacent the first magneto-resistance sensor chip, the second magneto-resistance sensor chip including at least one magneto-resistance sensor circuit. The position and orientation sensor package is constructed such that the at least one magneto-resistance sensor circuit of the first magneto-resistance sensor chip is oriented in a different direction than the at least one magneto-resistance sensor circuit of the second magneto-resistance sensor chip.

19 Claims, 5 Drawing Sheets

(51) Int. Cl.
*G01R 33/00* (2006.01)
*G01R 33/02* (2006.01)

(58) Field of Classification Search
CPC ...... G01B 15/00; G01D 5/16; G01R 33/0052; G01R 33/0206; G01R 33/0017; G01R 33/0005; G01R 15/185; G01R 33/34046; G01R 15/183; G01R 33/1284; G01R 33/4608; G01R 33/4828; G01R 33/485; G01R 33/5605; G01R 33/5607; G01R 15/18; G01R 19/0092; G01R 33/288; G01R 33/34084; G01R 33/341; G01R 33/3415; G02F 1/095; G02F 1/0115; G02F 1/011; G02F 1/0955; G02F 2202/32; G02F 1/0136; G02F 2203/12; G02F 2203/48; G02F 1/093; G02F 1/01; G02F 1/0126; G02F 1/0316; G02F 1/035; G02F 1/225; G02F 1/29; G02F 2201/02; G02F 2201/06; G02F 2201/30; G02F 2202/36; G02F 2203/06; G02F 2203/10; H02J 7/025; H02J 7/0042; H02J 50/70; H02J 50/90; H02J 17/00; H02J 50/20
See application file for complete search history.

(56) References Cited

U.S. PATENT DOCUMENTS

| | | | |
|---|---|---|---|
| 6,304,082 | B1 | 10/2001 | Gualtieri et al. |
| 6,376,933 | B1* | 4/2002 | Goetz .................. G01R 33/09 307/91 |
| 8,018,229 | B1 | 9/2011 | Horning et al. |
| 8,750,961 | B1* | 6/2014 | Ries .................. A61N 1/3718 600/407 |
| 2005/0122100 | A1 | 6/2005 | Wan et al. |
| 2007/0035294 | A1 | 2/2007 | Peczalski et al. |
| 2007/0080682 | A1 | 4/2007 | Govari et al. |
| 2011/0074406 | A1 | 3/2011 | Mather et al. |
| 2011/0234218 | A1 | 9/2011 | Lagouge |
| 2012/0206137 | A1 | 8/2012 | Cai et al. |
| 2012/0313193 | A1 | 12/2012 | Rieger et al. |
| 2014/0005517 | A1 | 1/2014 | Nagarkar et al. |
| 2014/0015525 | A1 | 1/2014 | Paci et al. |
| 2014/0062469 | A1 | 3/2014 | Yang et al. |
| 2014/0138346 | A1 | 5/2014 | Whig et al. |
| 2014/0188422 | A1 | 7/2014 | Huber et al. |
| 2014/0225605 | A1 | 8/2014 | Lei et al. |
| 2014/0292312 | A1 | 10/2014 | Chen et al. |

* cited by examiner

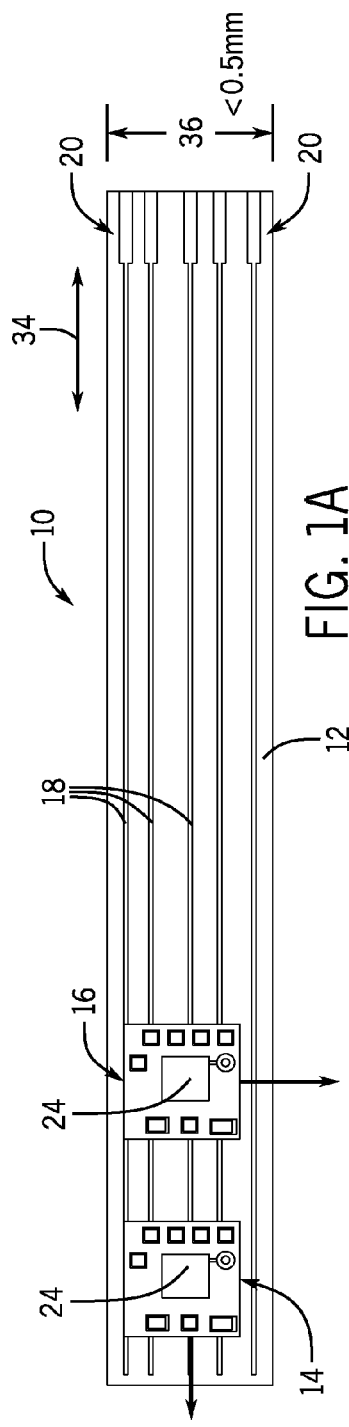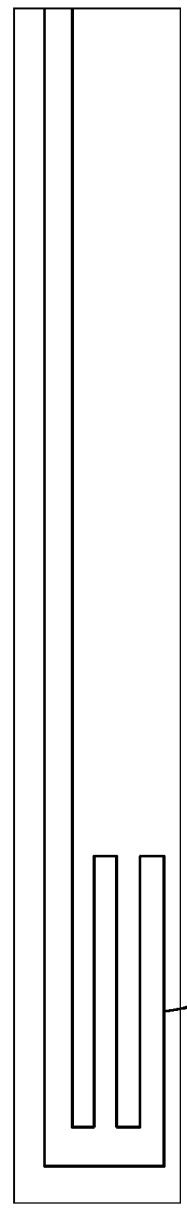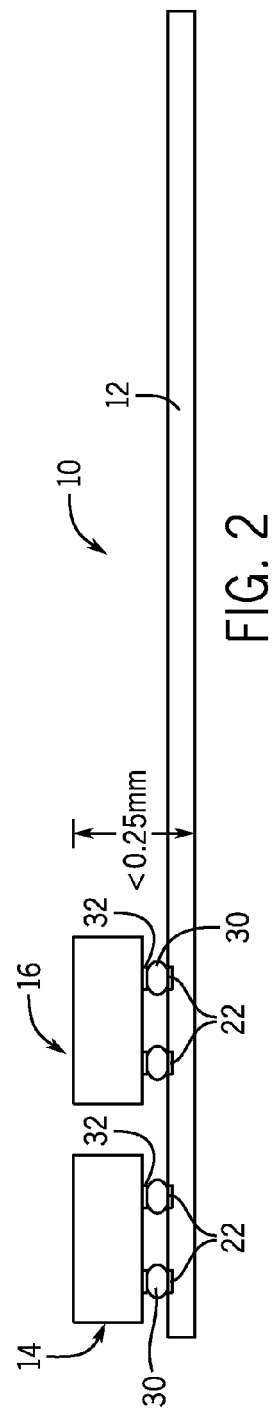

MULTI-AXIS MAGNETO-RESISTANCE SENSOR PACKAGE

BACKGROUND OF THE INVENTION

Embodiments of the invention relate generally to sensors that may be used to provide position/orientation information for an instrument, implant, or device used in a medical context, such as in a surgical or interventional context, and, in particular, to multi-axis packaged magneto-resistance sensors.

In various medical contexts it may be desirable to acquire position and/or orientation information for a medical instrument, implant, or device that is navigated or positioned (externally or internally) relative to a patient. For example, in surgical and/or interventional contexts, it may be useful to acquire position and/or orientation information for a medical device, or portion of a medical device, even when the device or relevant portion is otherwise out of view, such as within a patient's body. Likewise, in certain procedures where an imaging technique is used to observe all or part of the position and orientation information, it may be useful to have position and orientation information derived from the tracked device itself that can be related to other data, such as image data that may be contemporaneously acquired.

In such medical contexts, electromagnetic (EM) sensors may be implemented to provide the position/orientation information for the medical instrument, implant, or device. The EM sensors may be utilized as part of a position/orientation tracking system that includes a controller, a magnetic field source transmitter that generates a magnetic field with spatially varying characteristics (so the field is different at different locations), and an EM sensor that is integrated with the medical instrument, implant or device being tracked. The position of the EM sensor may be determined by calculating the position where the EM sensor observations agree with the calculated magnetic field from the transmitter—i.e., by measuring the mutual inductance between the transmitter and the EM sensor and processing the measured values to resolve a position and orientation of the EM sensor relative to the transmitter.

One issue that can arise with respect to navigation sensors suitable for acquiring position and orientation information in this manner is the size of the position and orientation sensor relative to the device that is to be tracked. In particular, in surgical and interventional contexts, it may be desired to use an instrument, implant or device that is as small as possible, either due to the size and/or fragility of the anatomy undergoing the procedure or to otherwise minimize the trauma associated with the procedure. Therefore, it may also be desirable to use a navigation sensor that is suitably sized for the instruments, implants or devices being employed. However, it may be difficult to construct a suitable position and orientation sensor assembly that provides the desired position and orientation information with the desired precision and accuracy and which is of a suitable size for use with or within the instruments, implants or devices in question. For example, existing position and orientation sensor assemblies may often be structured as a single chip containing two orthogonally placed sense circuits, a calibration coil, and an initialization coil, with such assemblies being approximately 1 mm$^2$ in size. While this size position and orientation sensor assembly is useable in many applications in the neural, cardiac, and orthopedic spaces, it cannot be integrated into many standard catheter lumens and needles that are smaller than 1 mm.

Therefore, it is desirable to provide a position and orientation sensor assembly whose size is reduced as compared to existing position and orientation sensor assembly options. It is further desirable that such a position and orientation sensor assembly would still provide position and orientation information with adequate precision and accuracy and with sensing in six degrees of freedom.

BRIEF DESCRIPTION OF THE INVENTION

In accordance with one aspect of the invention, a position and orientation sensor package includes a dielectric substrate and a first magneto-resistance sensor chip attached to the dielectric substrate, the first magneto-resistance sensor chip comprising at least one magneto-resistance sensor circuit. The position and orientation sensor package also includes a second magneto-resistance sensor chip attached to the dielectric substrate and positioned adjacent the first magneto-resistance sensor chip, the second magneto-resistance sensor chip comprising at least one magneto-resistance sensor circuit. The at least one magneto-resistance sensor circuit of the first magneto-resistance sensor chip is oriented in a different direction than the at least one magneto-resistance sensor circuit of the second magneto-resistance sensor chip.

In accordance with another aspect of the invention, a method of manufacturing a position and orientation sensor package includes providing a dielectric substrate and attaching a first magneto-resistance sensor chip to the dielectric substrate, the first magneto-resistance sensor chip comprising at least one magneto-resistance sensor circuit. The method also includes attaching a second magneto-resistance sensor chip to the dielectric substrate such that the second magneto-resistance sensor chip is positioned adjacent the first magneto-resistance sensor chip, the second magneto-resistance sensor chip comprising at least one magneto-resistance sensor circuit. The first and second magneto-resistance sensor chips are attached to the dielectric substrate to establish a known angle between the at least one magneto-resistance sensor circuit of the first magneto-resistance sensor chip and the at least one magneto-resistance sensor circuit of the second magneto-resistance sensor chip.

In accordance with yet another aspect of the invention, a multi-axis magneto-resistance sensor package includes a flex circuit comprising a dielectric substrate and conductive interconnects, a first magneto-resistance sensor chip attached to the dielectric substrate so as to be electrically coupled to the conductive interconnects, and a second magneto-resistance sensor chip attached to the dielectric substrate so as to be electrically coupled to the conductive interconnects. Each of the first and second magneto-resistance sensor chips includes at least one magneto-resistance sensor circuit, with the first and second magneto-resistance sensor chips being attached to the flex circuit such that an orientation of the at least one magneto-resistance sensor circuit on the first magneto-resistance sensor chip is different from an orientation of the at least one magneto-resistance sensor circuit on the second magneto-resistance sensor chip by a known angle.

Various other features and advantages will be made apparent from the following detailed description and the drawings.

BRIEF DESCRIPTION OF THE DRAWINGS

The drawings illustrate embodiments presently contemplated for carrying out the invention.

In the drawings:

FIGS. 1A and 1B depict top and bottom views, respectively, of a position and orientation sensor package in accordance with an embodiment of the invention.

FIG. 2 depicts a side view of the position and orientation sensor package of FIGS. 1A and 1B.

DETAILED DESCRIPTION

Figure 3:
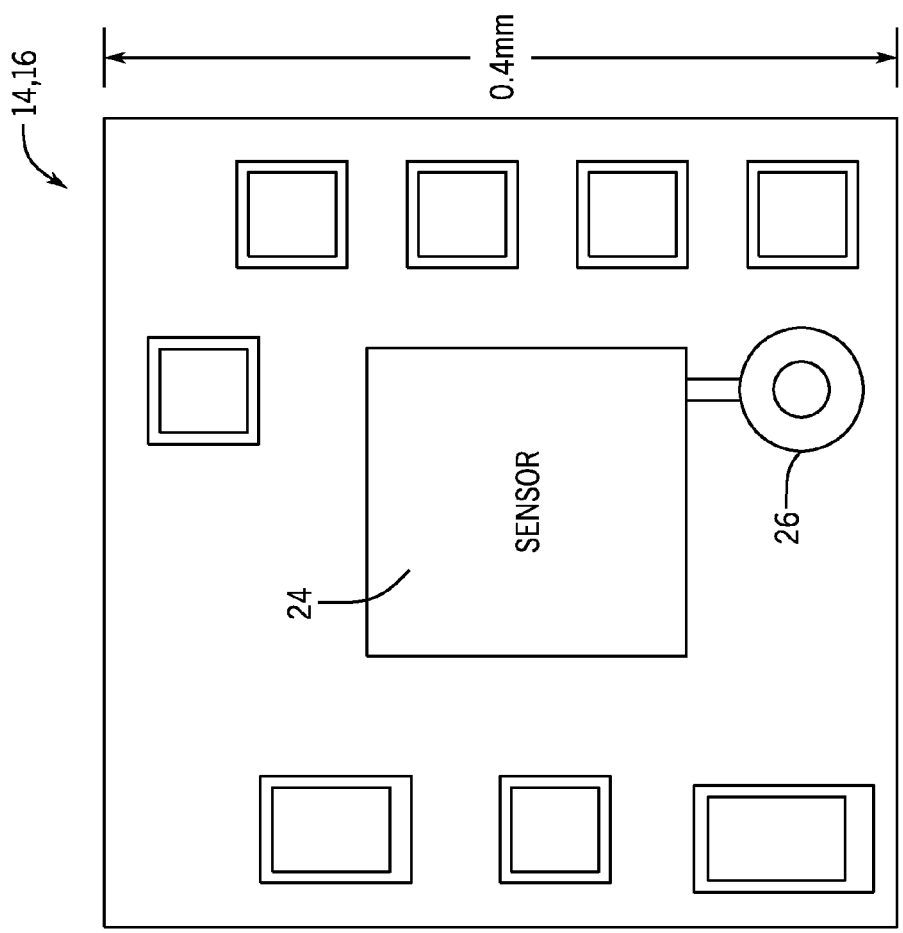
FIG. 3 depicts a magneto-resistance sensor chip useable in the position and orientation sensor package of FIGS. 1A and 1B and FIG. 2 in accordance with an embodiment of the invention.

Embodiments of the invention provide a multi-axis magneto-resistance sensor package that provides position/orientation information. The package includes a number of chips that each contains one or more sense circuits formed thereon, with the chips mounted on a common substrate in a manner that reduces the size of the package in at least one dimension as compared to existing position and orientation sensor assemblies.

As discussed herein, components of a position/orientation system may generally be attached to various types of surgical or interventional instruments, implants, devices, or any other suitable device for which position and orientation information may be desired during surgical or interventional contexts. The position/orientation system is suitable for correcting and tracking the position and orientation of the various surgical or interventional devices. In particular, in certain embodiments disclosed herein, the position/orientation system includes a plurality of electromagnetic (EM) sensors that measure or respond to an external magnetic field and which may be used to determine spatial properties, such as position coordinates and/or orientation (i.e., angular) information. In an exemplary embodiment, the EM sensors may be a one one-axis or two-axis magneto-resistance sensors configured to generate position and orientation information in the presence of an externally applied magnetic field.

Referring now to FIGS. 1A and 1B and FIG. 2, a multi-axis magneto-resistance sensor package 10 that provides position and orientation information (i.e., a position and orientation sensor package) is illustrated according to an embodiment of the invention. The package 10 generally includes a dielectric substrate 12 and an arrangement of a first magneto-resistance sensor chip 14 and a second magneto-resistance sensor chip 16 attached to the substrate 12. A known attachment/packaging technique may be utilized to attach the first and second magneto-resistance sensor chips 14, 16 to the substrate 12 (as will be explained in greater detail below), with electrical connectivity being provided between the chips 14, 16 and the substrate 12 such that leads or interconnects 18 formed on or in the substrate 12 (i.e., forming a "flex circuit") can receive signals from the chips 14, 16 and route the signals to an input/output (I/O) 20 of the package 10.

According to embodiments of the invention, the substrate 12 of package 10 is formed of a dielectric material that is chosen to provide mechanical stability to the package during use, as well as provide suitable dielectric properties. Accordingly, the dielectric substrate 12 may be formed of any of a number of suitable dielectric materials, including a ceramic (e.g., BaTi (barium titanium)), FR4, polyimide or a polymer film (e.g., Kapton®, Ultem®, polytetrafluoroethylene (PTFE), Upilex®), according to embodiments of the invention. A plurality of connection pads 22 are formed on the substrate 12 to provide for mechanical and electrical connection of the magneto-resistance sensor chips 14, 16 to the substrate, with leads/interconnects 18 being running out from the connection pads 22 and being formed on the substrate 12 via any of a number of known techniques. According to various embodiments, the leads/interconnects 18 may be formed as traces on the surface of the substrate 12 to provide electrical pathways on the package 10. For example, the interconnects 18 may be formed via application of an initial sputtered adhesion layer (titanium, chromium, etc.) and a sputtered copper seed layer, on which additional copper can be plated. The interconnects 18 may be patterned and etched to a desired shape, such as to provide for electrical connections between the connection pads 22 and I/O connections 20 of the package. Additional features such as vias (not shown) may also be formed in substrate 12, with the interconnects 18 being formed in the vias and out onto the surface of the substrate 12 to increase routing options in the package 10.

According to an embodiment of the invention, the first and second magneto-resistance sensor chips 14, 16 of package 10 are solid-state (i.e., silicon based) devices that include circuitry thereon that provides for determination of a position and orientation of the chip. More specifically, each of the first and second magneto-resistance sensor chips 14, 16 may be formed to have one or more magneto-resistance sensor circuits 24 (or miniature surface mount sensors) thereon. The one or more magneto-resistive sensor circuits 24 each generate signals indicative of a change in electrical resistance of a conductor or semiconductor when a magnetic field is applied and the sensor circuit 24 moves or changes orientation with respect to the externally applied magnetic field. That is, in sensor chips 14, 16, the chip's resistance at various sensor circuits 24 depends upon the magnetic field applied. According to embodiments of the invention, each of the first and second magneto-resistance sensor chips 14, 16 may include a single magneto-resistance sensor circuit 24 formed thereon or may include two magneto-resistance sensor circuits 24 formed thereon.

Figure 4:
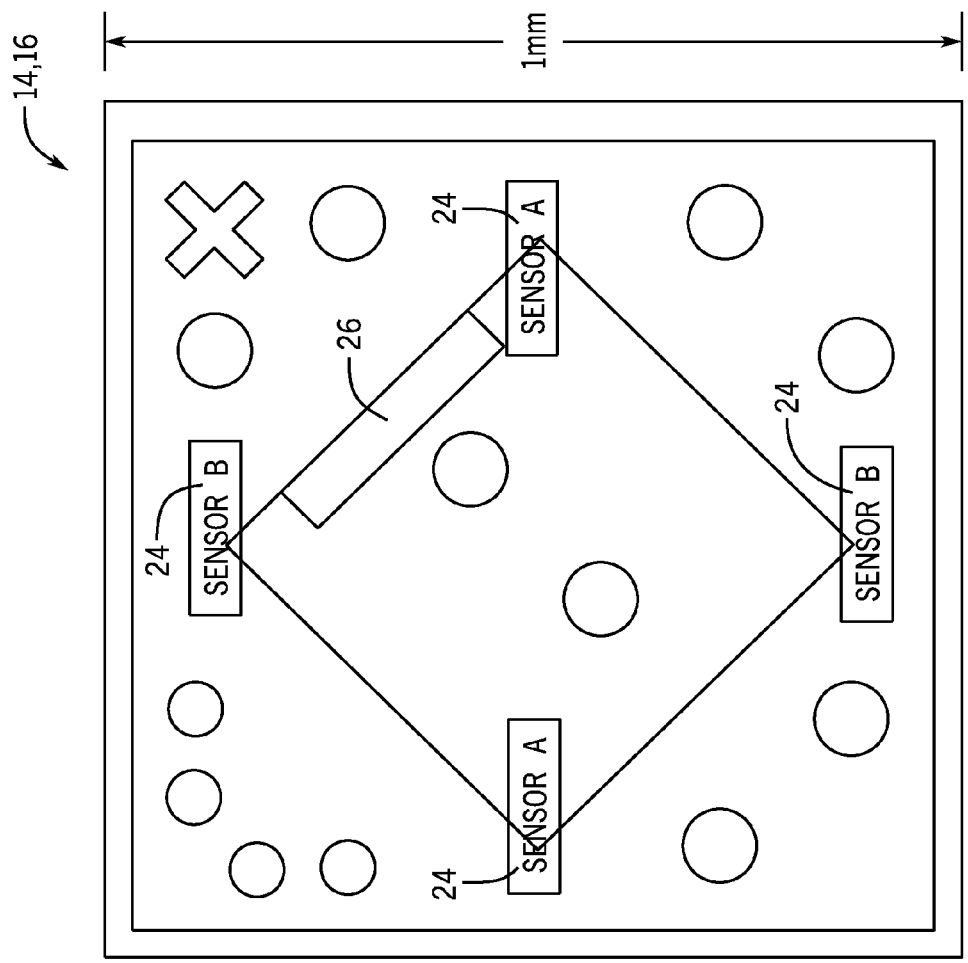
FIG. 4 depicts a magneto-resistance sensor chip useable in the position and orientation sensor package of FIGS. 1A and 1B and FIG. 2 in accordance with an embodiment of the invention.

Turning to FIG. 3 and, enlarged top views of a magneto-resistance sensor chip 14, 16 are illustrated—with FIG. 3 being directed to a sensor chip that includes thereon only a single magneto-resistance sensor circuit 24 (i.e., a one-axis sensor) and with FIG. 4 being directed to a sensor chip 14, 16 that includes thereon two magneto-resistance sensor circuits 24 (i.e., a two-axis sensor) arranged orthogonal to one another. The sensor circuit(s) 24 are sufficiently sensitive to generate position (i.e., x, y, and/or z position data) and orientation data (i.e., roll, pitch, and yaw orientation data) in the presence of a magnetic field. In certain implementations, the magneto-resistance sensor chips 14, 16 operate at a low voltage (e.g., 2.0 V or less) and over a wide magnetic field range (e.g., ±10 Oe). Further, in certain implementations the magneto-resistance sensor chips 14, 16 have a very low noise floor at metal tolerant frequencies (e.g., 10-1000 times lower than microcoils).

The dimensions and sizing of the magneto-resistance sensor chip 14, 16 is determinant largely based on whether the chip is formed as a one-axis or two-axis sensor. The one-axis sensor chip of FIG. 3 that includes one a single magneto-resistance sensor circuit 24 may, for example, have dimensions of 0.4 mm×0.4 mm to 0.5 mm×0.5 mm, while the two-axis sensor chip of FIG. 4 that includes a pair of orthogonally arranged magneto-resistance sensor circuits 24 may, for example, have dimensions of 0.9 mm×0.9 mm to 1.0 mm×1.0 mm. Accordingly, it can be seen that compact form factor of the one-axis sensor chip may provide for implementation thereof with certain instruments or devices (e.g., catheter lumens, needles, etc.) in which a two-axis sensor chip may not be feasible.

In practice, the magneto-resistance sensor chips 14, 16 may be a multi-layer design, such as having layers corresponding to (in one embodiment) an offset or calibration coil 26 used to calibrate the sensor chip, a set-reset strap (not shown) allowing the magnetic sensor circuit(s) 24 to be reset, and a resistor bridge (not shown) used to measure the magnetic field. In one implementation, the calibration coil 26 is formed as a metallic coil that may be used for dynamic calibration operations in order to reduce the errors in position and/or orientation resulting from unpredictable variations in the environment in which the magneto-resistance sensor chip 14, 16 operates relating to temperature, magnetic field, and the like. In particular, the calibration coil 26 is configured to generate known magnetic field at a specified frequency, which may then be extrapolated to calibrate the sensor chip 14, 16 at other frequencies. In certain embodiments, a calibration system provides an initial calibration prior to operating the sensor chip 14, 16, or a single calibration at the location where the sensor chip is in operation, while in other embodiments, the calibration system may function as part of a feedback loop used to calibrate the sensor chip 14, 16 during use, continuously or intermittently. In some embodiments, the calibration coil 26 calibrates the magneto-resistance sensor chip 14, 16 based on the structural design of the calibration coil 26 in relation to the sensor circuit(s) 24. For example, the calibration coil 26 may be at a fixed position in relation to the two sensor circuits 24 of two-axis magneto-resistance sensor chip 14, 16 (FIG. 4). As such, the external magnetic field relative to the electrical resistance generated (e.g., B/I value) by the calibration coil 26 is always constant. Furthermore, the B/I value is a geometric quantity that is independent of the excitation current (e.g., which may create the electrical resistance) generated by the magneto-resistance sensor chip 14, 16. It may be useful to use the B/I value in an algorithm for calibrating the magneto-resistance sensor chip 14, 16 because the B/I value of the calibration coil 26 generally does not change with temperature, magnetic field, or similar variations in the magneto-resistance sensor chip environment.

In one embodiment, and alternative to the first and second magneto-resistance sensor chips 14, 16 each having its own calibration coil 26 as shown and described in FIGS. 3 and 4, it is recognized that package 10 could include a common calibration coil 28 used to calibrate each of the first and second magneto-resistance sensor chips 14, 16. Referring back to FIG. 1B, it is shown therein that a common calibration coil 28 is provided in package 10 that is formed on substrate 12 and is connected to package I/O connections 20. In an exemplary embodiment, the common calibration coil 28 is formed on a side of substrate 12 opposite from the side that the first and second magneto-resistance sensor chips 14, 16 are attached. The common calibration coil 28 may be at a fixed position in relation to the sensor circuits 24 of the magneto-resistance sensor chips 14, 16, such that the external magnetic field relative to the electrical resistance generated by the common calibration coil 28 is always constant. Beneficially, use of common calibration coil 28 in package 10 for both of the sensor chips 14, 16 reduces the number of leads/interconnects 18 required in package 10 (as compared to leads/interconnects that would be required for a separate calibration coil for each sensor chip 14, 16). Additionally, use of the common calibration coil 28 in package 10 conserves current, with the current associated with use of the common calibration coil 28 having to be measured only once, as compared to twice if/when separation calibration coils are employed.

In utilizing the first and second magneto-resistance sensor chips 14, 16 for determination of a position and orientation of the multi-axis magneto-resistance sensor package 10, it is necessary that that the magneto-resistance sensor circuit(s) 24 of the respective first magneto-resistance sensor chip 14 be oriented in a different direction than the magneto-resistance sensor circuit(s) 24 of the second magneto-resistance sensor chip 16 in order that the package 10 is able to generate position (i.e., x, y, and/or z position data) and orientation data (i.e., roll, pitch, and yaw orientation data) in the presence of a magnetic field. Thus, in an embodiment where each of the first and second magneto-resistance sensor chips 14, 16 comprises a one-axis sensor that includes only a single sensor circuit 24, the sensor circuit 24 of the first magneto-resistance sensor chip 14 will be oriented in a different direction than the sensor circuit 24 of the second magneto-resistance sensor chip 16. In an exemplary embodiment, and as shown in FIG. 1A, the first and second magneto-resistance sensor chips 14, 16 are attached to the substrate 12 such that their respective sensor circuits 24 are oriented orthogonal to one another (i.e., oriented 90° relative to one another).

While the multi-axis magneto-resistance sensor package 10 illustrated in FIGS. 1A, 1B and 2 is constructed such that the sensor circuits 24 of the first and second magneto-resistance sensor chips 14, 16 are oriented orthogonal to one another, it is recognized that the sensor circuits 24 of the chips 14, 16 may be oriented relative to one another at angles other than 90°. That is, package 10 is able to function to generate position and orientation data in the presence of a magnetic field with the sensor circuits 24 oriented relative to one another at angles other than 90°—with the important limitation being that the orientation between the magneto-resistance sensor circuit 24 of each of the first and second magneto-resistance sensor chips 14, 16 be known and controlled during assembly of the package 10. With the angle between the sensor circuits 24 of the first and second magneto-resistance sensor chips 14, 16 being known, signals generated by the sensor circuits 24 can be processed to accurately determine position and orientation of the package 10.

With regard to the attachment of the first and second magneto-resistance sensor chips 14, 16 to the substrate 12 in order to provide a known orientation/angle between the sensor circuits 24 of the first and second magneto-resistance sensor chips 14, 16, an exemplary embodiment of the invention is directed to attachment of the first and second magneto-resistance sensor chips 14, 16 to the substrate 12 via a flip-chip application. As shown in FIG. 2, in attaching the first and second magneto-resistance sensor chips 14, 16 to the substrate 12 via a flip-chip process, a small dot of solder 30 is deposited on chip pads 32 of the magneto-resistance sensor chips 14, 16 (corresponding to sensor inputs and outputs for the sensor circuit(s), set-reset operations for the sensor circuit(s), offset or calibration operations for the sensor circuit(s), power, ground, etc.) near the end of the manufacturing process thereof. The first and second magneto-resistance sensor chips 14, 16 are then attached to the substrate 12 by inverting the chips to bring the solder bumps 30 down onto the connections pads 22 of the underlying substrate 12. The solder bumps 30 are then re-melted to produce an electrical connection, typically using a reflow solder process or alternatively a thermosonic bonding, with an electrically-insulating adhesive (not shown) then typically being "underfilled" in a remaining gap between the chip's circuitry and the underlying mounting substrate 12 to provide a stronger mechanical connection, provide a heat bridge, and to ensure the solder joints are not stressed due to differential heating of the chip 14, 16 and the rest of the package 10. By use of a flip-chip application, the positional accuracy of the placement/attachment of the first and second magneto-resistance sensor chips 14, 16 on the substrate 12 can be controlled within 0.25° such that the orientation/angle between the sensor circuits 24 of the first and second magneto-resistance sensor chips 14, 16 can be sufficiently known and controlled.

As shown in FIGS. 1A, 1B and 2, with further regard to the attachment of the first and second magneto-resistance sensor chips 14, 16 to the substrate 12, it can be seen that the first and second magneto-resistance sensor chips 14, 16 are positioned thereon so as to minimize the size of the package 10 in one dimension. That is, the first and second magneto-resistance sensor chips 14, 16 are attached to the substrate 12 so as to be adjacent to one another, with the first and second magneto-resistance sensor chips 14, 16 being along a lengthwise direction (indicated by arrow 34) of the dielectric substrate such that a width of the package (indicated by arrow 36) is minimized. In an embodiment where each of the first and second magneto-resistance sensor chips 14, 16 are constructed as one-axis sensors (i.e., each chip includes only a single magneto-resistance sensor circuit 24), the width of the overall package 10 may thus be kept down to approximately 0.5 mm (and the height of the package to approximately 0.25 mm)—which allows for placement of the package 10 in medical devices/instruments such as catheter lumens and fine needles, for example.

Figure 5:
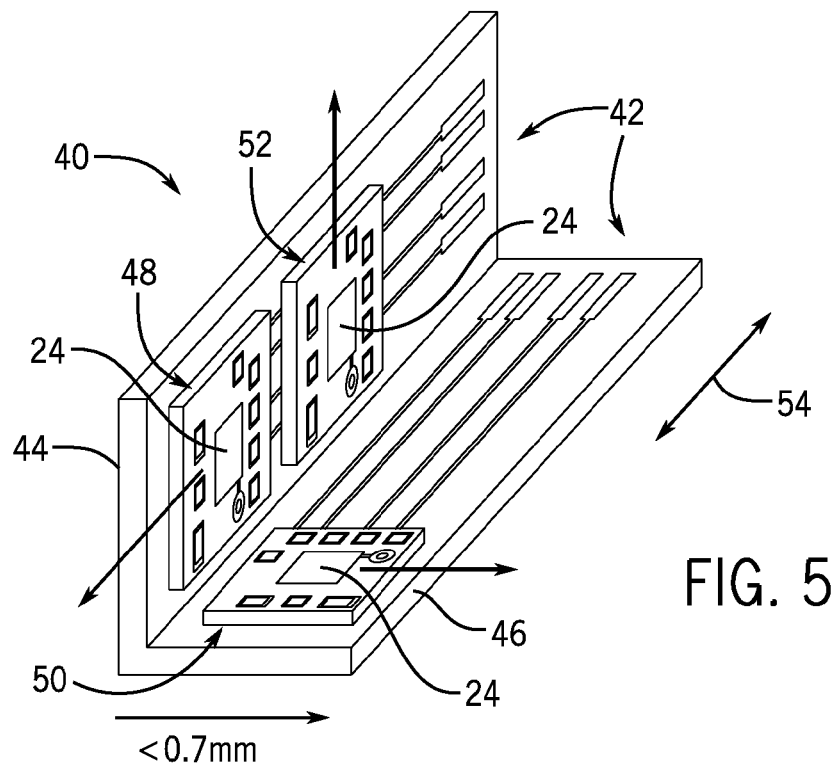
FIGS. 5 and 6 depict a position and orientation sensor package in accordance with another embodiment of the invention.
Figure 6:
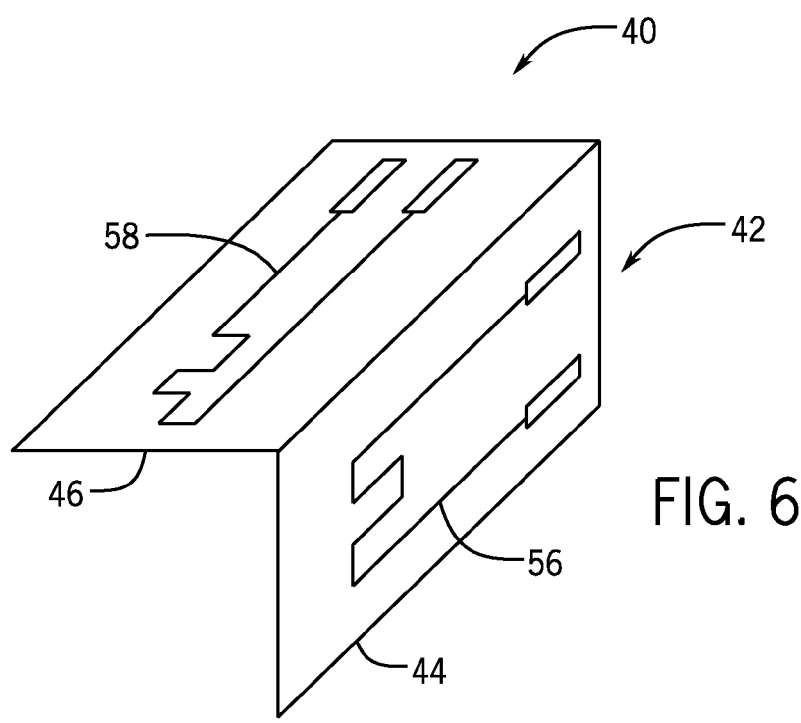

Referring now to FIGS. 5 and 6, a multi-axis magneto-resistance sensor package 40 that provides position and orientation information is illustrated according to another embodiment of the invention, with the package 40 being constructed as a three-axis package. The package 40 is similar in function/operation to the package 10 shown and described in FIGS. 1A, 1B and 2, except that the construction of a dielectric substrate 42 therein provides for an arrangement of magneto-resistance sensor chips thereon such that sensor circuits of the chips may be arranged/oriented along three axes in order to provide a three-axis sensing package. As shown in FIGS. 5 and 6, the substrate 42 is formed of a first substrate portion 44 positioned along a first plane and a second substrate portion 46 positioned along a second plane that is orthogonal to the first plane—such that the substrate 42 has an L-shaped construction.

According to embodiments of the invention, the number of magneto-resistance sensor chips included in the three-axis magneto-resistance sensor package 40 may vary based on the type of chips included in the package—i.e., whether the chips are configured as one-axis sensors or two-axis sensors.

In an exemplary embodiment, and as shown in FIG. 5, a plurality of one axis sensors are included in the package 40—with each of a first magneto-resistance sensor chip 48, a second magneto-resistance sensor chip 50, and a third magneto-resistance sensor chip 52 being provided as a one-axis sensor that includes a single sensor circuit 24 thereon (although it is recognized that the second magneto-resistance sensor chip could instead be a two-axis sensor). The first and third magneto-resistance sensor chips 48, 52 are attached to the first substrate portion 44 so as to be adjacent one another and aligned in a lengthwise direction (indicated by arrow 54) of the substrate 42, while the second magneto-resistance sensor chip 50 is attached to the second substrate portion 46 at a location so as to be adjacent to one of the first and third magneto-resistance sensor chips 48, 52. The first, second, and third magneto-resistance sensor chips 48, 50, 52 are attached to the substrate portions 44, 46 such that the sensor circuit 24 on each chip is oriented at a different angle than the other respective sensor circuits 24—with an exemplary embodiment attaching the chips 48, 50, 52 to the substrate portions 44, 46 such that the sensor circuits 24 are oriented orthogonally to each other. However, as set forth in detail above, it is recognized that the sensor circuits 24 of chips 48, 50, 52 could be oriented relative to one another at angles other than 90°, as long as the orientation between the magneto-resistance sensor circuit 24 of each of the chips 48, 50, 52 is known (i.e., controlled during assembly of the package)—with a flip-chip manufacturing and placement technique being used to attach the first, second, and third magneto-resistance sensor chips 48, 50, 52 to the substrate 42 in order to control the positional accuracy of the chips on the substrate to within 0.25° of a desired orientation.

In other embodiments, the number of magneto-resistance sensor chips included in the three-axis magneto-resistance sensor package 40 can be less than the three chips 48, 50, 52 illustrated in FIGS. 5 and 6. For example, the three-axis magneto-resistance sensor package 40 could be constructed to include only two magneto-resistance sensor chips—with a first magneto-resistance sensor chip attached to the first substrate portion 44 and being in the form of a two-axis sensor (two orthogonally oriented sensor circuits thereon) and with a second magneto-resistance sensor chip attached to the second substrate portion 46 and being in the form of a one-axis or two-axis sensor with at least one sensor circuit thereon oriented differently (e.g., orthogonally) from the two sensor circuits of the first magneto-resistance sensor chip.

As shown in FIG. 6, the package 10 further includes a number of common calibration coils 56, 58 used to calibrate the first, second, and third magneto-resistance sensor chips 48, 50, 52. A common calibration coil 56 may be provided on the first substrate portion 44 (on a back side thereof) for calibrating the first and third magneto-resistance sensor chips 48, 52, while a separate common calibration coil 58 may be provided on the second substrate portion 46 (on a back side thereof) for calibrating the second magneto-resistance sensor chip 50. The calibration coils 56, 58 may be used for dynamic calibration operations in order to reduce the errors in position and/or orientation resulting from unpredictable variations in the environment in which the magneto-resistance sensor chips 48, 50, 52 operate relating to temperature, magnetic field, and the like—with the calibration coils 56, 58 configured to generate a known magnetic field at a specified frequency, which may then be extrapolated to calibrate the sensor circuits 24 at other frequencies.

Figure 7:
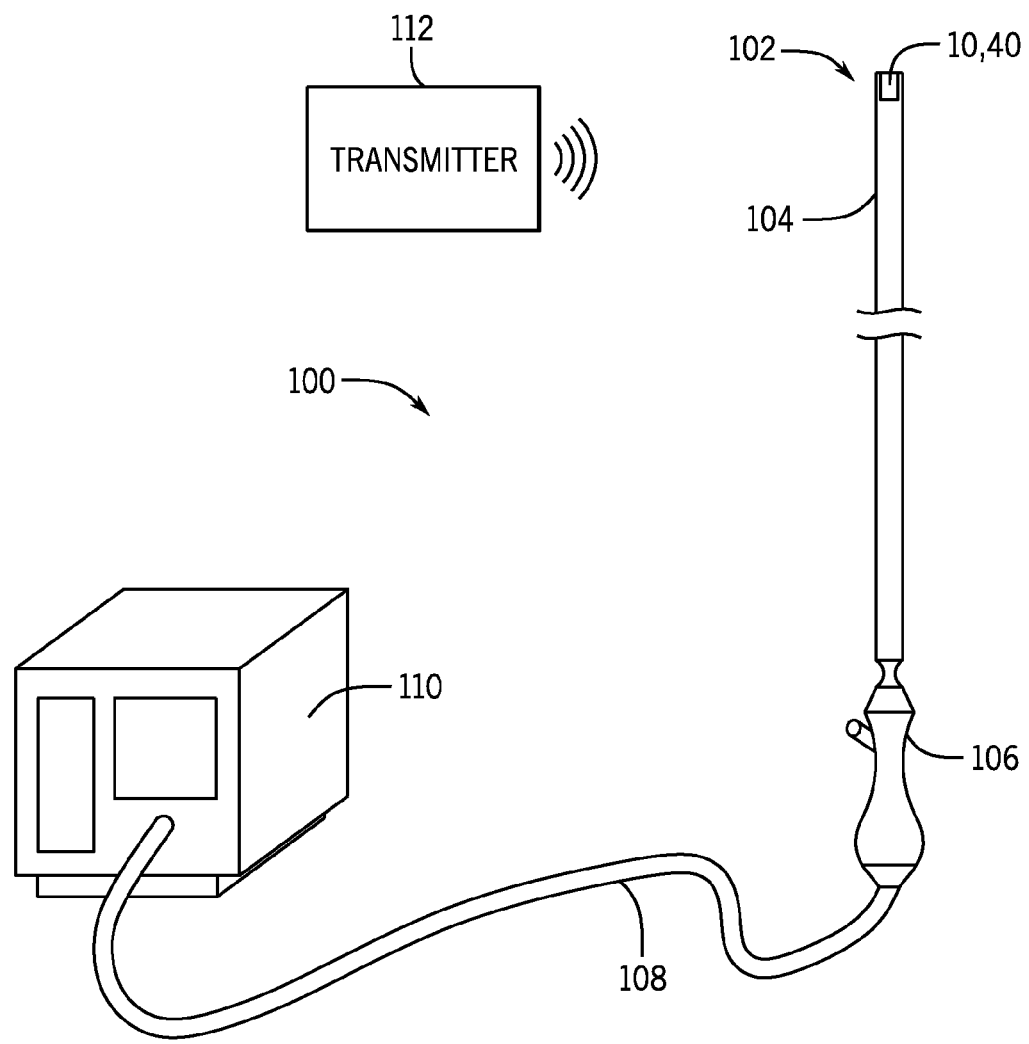
FIG. 7 depicts an example of an interventional device in which a position and orientation sensor package may be incorporated in accordance with an embodiment of the invention.

Referring now to FIG. 7, an example of a medical device 100 that is suitable for use with a multi-axis magneto-resistance sensor package 10 (FIG. 1) is shown. In this example, the medical device 100 is a catheter suitable for insertion into and navigation through the vasculature of a patient. Though a catheter is provided by way of example, the multi-axis magneto-resistance sensor packages 10, 40 discussed herein may be provided on or in various other types of surgical or interventional instruments, implants or devices. Examples of such instruments, implants or devices include, but are not limited to: implant, probe, awl, drill, aspirator, forceps, blade, screw, nail, pin, k-wire, needle, cannula, introducer, catheter, guidewire, stent, heart valve, filter, endoscope, laparoscope, or electrode, endoscopes or other intrabody camera devices, or any other suitable device for which position and orientation information may be desired during surgical or interventional use.

The depicted medical device 100 (e.g., catheter) includes a distal end or tip 102 in which a multi-axis magneto-resistance sensor package 10, 40 may be positioned. In one embodiment, the multi-axis magneto-resistance sensor package may be a two-axis magneto-resistance sensor package 10 configured to generate position and orientation information in the presence of an externally applied magnetic field, as shown and described in FIGS. 1A, 1B and 2. In another embodiment, the multi-axis magneto-resistance sensor package may be a three-axis magneto-resistance sensor package 40 configured to generate position and orientation information in the presence of an externally applied magnetic field, as shown and described in FIGS. 5 and 6. A shaft 104 is in communication with the tip 102, and the shaft 104 connects the tip 102 with a handle assembly 106 that may be used to manipulate and operate the medical device 100 (e.g., catheter). In certain instances, the handle assembly 106 may communicate, such as via cable 108, with an operator console 110 that allows a user to control certain aspects of the catheter function and operation.

In operation, a magnetic field transmitter 112 associated with the medical device 100 (and fixed in a known position in relation to the medical device 100) transmits a magnetic field having spatially varying characteristics over a volume that includes sensor package 10, 40. While transmitter 112 is shown in FIG. 7 as a single transmitter element, it is recognized that several transmitters at spaced apart locations may be utilized for generating magnetic fields sensed by the sensor package 10, 40, according to other embodiments. The magnetic field generated by the transmitter 112 is sensed by the sensor chips of the multi-axis magneto-resistance sensor package 10, 40 (i.e., the strength of the magnetic field) is used to determine the spatial properties of the medical device 100, for example, the position (e.g., the X-, Y-, and Z-coordinates) and orientation (e.g., the pitch, yaw, and roll angles). Signals acquired from the multi-axis magneto-resistance sensor package 10, 40 in the medical device 100 may be processed to generate position/orientation information related to the medical device 100, such as via processing circuitry and/or memory in the console 110.

Beneficially, embodiments of the invention thus provide a multi-axis magneto-resistance sensor package that provides position/orientation information. The package includes a number of chips that each contains one or more sense circuits formed thereon, with the chips mounted on a common substrate in a manner that reduces the size of the package in at least one dimension as compared to existing position and orientation sensor assemblies. In manufacturing the package, the chips are attached to the substrate using a controlled placement technique, such that the orientation of the magneto-resistance sensor circuit on a respective chip relative to the magneto-resistance sensor circuit of one or more other respective chips is known.

Therefore, according to one embodiment of the invention, a position and orientation sensor package includes a dielectric substrate and a first magneto-resistance sensor chip attached to the dielectric substrate, the first magneto-resistance sensor chip comprising at least one magneto-resistance sensor circuit. The position and orientation sensor package also includes a second magneto-resistance sensor chip attached to the dielectric substrate and positioned adjacent the first magneto-resistance sensor chip, the second magneto-resistance sensor chip comprising at least one magneto-resistance sensor circuit. The at least one magneto-resistance sensor circuit of the first magneto-resistance sensor chip is oriented in a different direction than the at least one magneto-resistance sensor circuit of the second magneto-resistance sensor chip.

According to another embodiment of the invention, a method of manufacturing a position and orientation sensor package includes providing a dielectric substrate and attaching a first magneto-resistance sensor chip to the dielectric substrate, the first magneto-resistance sensor chip comprising at least one magneto-resistance sensor circuit. The method also includes attaching a second magneto-resistance sensor chip to the dielectric substrate such that the second magneto-resistance sensor chip is positioned adjacent the first magneto-resistance sensor chip, the second magneto-resistance sensor chip comprising at least one magneto-resistance sensor circuit. The first and second magneto-resistance sensor chips are attached to the dielectric substrate to establish a known angle between the at least one magneto-resistance sensor circuit of the first magneto-resistance sensor chip and the at least one magneto-resistance sensor circuit of the second magneto-resistance sensor chip.

According to yet another embodiment of the invention, a multi-axis magneto-resistance sensor package includes a flex circuit comprising a dielectric substrate and conductive interconnects, a first magneto-resistance sensor chip attached to the dielectric substrate so as to be electrically coupled to the conductive interconnects, and a second magneto-resistance sensor chip attached to the dielectric substrate so as to be electrically coupled to the conductive interconnects. Each of the first and second magneto-resistance sensor chips includes at least one magneto-resistance sensor circuit, with the first and second magneto-resistance sensor chips being attached to the flex circuit such that an orientation of the at least one magneto-resistance sensor circuit on the first magneto-resistance sensor chip is different from an orientation of the at least one magneto-resistance sensor circuit on the second magneto-resistance sensor chip by a known angle.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A position and orientation sensor package comprising:
    a dielectric substrate comprising:
        a first substrate portion positioned along a first plane; and
        a second substrate portion positioned along a second plane orthogonal to the first plane;
    a first magneto-resistance sensor chip attached to the first substrate portion, the first magneto-resistance sensor chip comprising at least one magneto-resistance sensor circuit; and
    a second magneto-resistance sensor chip attached to the second substrate portion, the second magneto-resistance sensor chip comprising at least one magneto-resistance sensor circuit;
    wherein the at least one magneto-resistance sensor circuit of the first magneto-resistance sensor chip is oriented in a different direction than the at least one magneto-resistance sensor circuit of the second magneto-resistance sensor chip;
    wherein the dielectric substrate is bent at a location between the first magneto-resistance sensor chip and the second magneto-resistance sensor chip to define the first substrate portion and the second substrate portion; and
    wherein the dielectric substrate comprises a plurality of electrical leads formed thereon and connected to the first and second magneto-resistance sensor chips to receive and transmit signals therefrom.

2. The position and orientation sensor package of claim 1 wherein the first and second magneto-resistance sensor chips are attached to the dielectric substrate such that the orientation between the at least one magneto-resistance sensor circuit of each of the first and second magneto-resistance sensor chips is known.

3. The position and orientation sensor package of claim 1 further comprising a third magneto-resistance sensor chip that is attached to the first substrate portion adjacent to the first magneto-resistance sensor chip, the third magneto-resistance sensor chip comprising at least one magneto-resistance sensor circuit, and wherein the third magneto-resistance sensor chip is aligned with the first magneto-resistance sensor chip along a lengthwise direction of the dielectric substrate.

4. The position and orientation sensor package of claim 3 wherein the at least one magneto-resistance sensor circuit on each of the first, second, and third magneto-resistance sensor chips comprises a single magneto-resistance sensor circuit, with the first, second, and third magneto-resistance sensor chips forming a three-axis sensor package.

5. The multi-axis magneto-resistance sensor package of claim 4 wherein each of a height and a width of the multi-axis magneto-resistance sensor package is approximately 0.5 mm or less, based on each of the first, second, and third magneto-resistance sensor chips comprising a single magneto-resistance sensor circuit.

6. The position and orientation sensor package of claim 1 wherein the at least one magneto-resistance sensor circuit on one or more of the first and second magneto-resistance sensor chips comprises:
    a first magneto-resistance sensor circuit; and
    a second magneto-resistance sensor circuit arranged orthogonal to the first magneto-resistance sensor circuit;
    wherein the first and second magneto-resistance sensor chips thus comprise two-axis sensor chips, such that the position and orientation sensor package comprises a three-axis sensor package.

7. The position and orientation sensor package of claim 1 wherein each of the first and second magneto-resistance sensor chips comprises further comprises a calibration coil positioned a fixed distance from the at least one magneto-resistance sensor circuit, the calibration coil configured to generate a calibration magnetic field that provides for calibration of the respective magneto-resistance sensor chip.

8. The position and orientation sensor package of claim 1 further comprising a common calibration coil positioned a fixed distance from the at least one magneto-resistance sensor circuit on each of the first and second magneto-resistance sensor chips, the common calibration coil configured to generate a calibration magnetic field that provides for calibration of each of the first and second magneto-resistance sensor chips.

9. The position and orientation sensor package of claim 1 wherein the dielectric substrate comprises a plurality of connection pads formed thereon and wherein each of the first and second magneto-resistance sensor chips comprises a plurality of chip pads formed thereon; and
    wherein the position and orientation sensor package further comprises a solder that joins respective chip pads of the first and second magneto-resistance sensor chips to respective connection pads of the dielectric substrate via a flip chip attachment.

10. The position and orientation sensor package of claim 1 wherein the dielectric substrate comprises one of an FR4, ceramic, or polyimide material.

11. The multi-axis magneto-resistance sensor package of claim 1 wherein the dielectric substrate is bent along an entirety of a length thereof to define the first substrate portion and the second substrate portion.

12. The multi-axis magneto-resistance sensor package of claim 1 wherein the first magneto-resistance sensor chip comprises a single magneto-resistance sensor circuit and the second magneto-resistance sensor chip comprises two magneto-resistance sensor circuits arranged orthogonal to one another, such that a width of the multi-axis magneto-resistance sensor package is approximately 0.5 mm or less and a height of the multi-axis magneto-resistance sensor package is approximately 1.0 mm or less.

13. A method of manufacturing a position and orientation sensor package comprising:
    providing a dielectric substrate comprising a first substrate portion positioned along a first plane and a second substrate portion positioned along a second plane orthogonal to the first plane;
    attaching a first magneto-resistance sensor chip to the to the first substrate portion of the dielectric substrate, the first magneto-resistance sensor chip comprising at least one magneto-resistance sensor circuit; and
    attaching a second magneto-resistance sensor chip to the to the second substrate portion of the dielectric substrate, the second magneto-resistance sensor chip comprising at least one magneto-resistance sensor circuit;

wherein attaching the first and second magneto-resistance sensor chips to the dielectric substrate comprises attaching the first and second magneto-resistance sensor chips to the dielectric substrate to establish a known angle between the at least one magneto-resistance sensor circuit of the first magneto-resistance sensor chip and the at least one magneto-resistance sensor circuit of the second magneto-resistance sensor chip; and wherein the dielectric substrate comprises a flexible substrate that is bent at a location between the first magneto-resistance sensor chip and the first magneto-resistance sensor chip, with the dielectric substrate comprising a plurality of electrical leads formed thereon and connected to the first and second magneto-resistance sensor chips to receive and transmit signals therefrom.

14. The method of claim 13 wherein attaching the first and second magneto-resistance sensor chips to the dielectric substrate comprises a flip-chip attachment of the first and second magneto-resistance sensor chips to the dielectric substrate, with a reflow-solder providing an electrical connection between chip pads of the first and second magneto-resistance sensor chips and connection pads of the dielectric substrate.

15. The method of claim 13 further comprising attaching a third magneto-resistance sensor chip to the first substrate portion such that the third magneto-resistance sensor chip is aligned with the first magneto-resistance sensor chip along a lengthwise direction of the dielectric substrate, the third magneto-resistance sensor chip comprising at least one magneto-resistance sensor circuit;

wherein the first, second, and third magneto-resistance sensor chips form a three-axis sensor package.

16. The method of claim 13 further comprising forming a common calibration coil on the dielectric substrate, the common calibration coil being positioned a fixed distance from the at least one magneto-resistance sensor circuit on each of the first and second magneto-resistance sensor chips, the common calibration coil configured to generate a calibration magnetic field that provides for calibration of each of the first and second magneto-resistance sensor chips.

17. A multi-axis magneto-resistance sensor package comprising:
a flex circuit comprising a dielectric substrate and conductive interconnects;
a first magneto-resistance sensor chip attached to the dielectric substrate so as to be electrically coupled to the conductive interconnects; and
a second magneto-resistance sensor chip attached to the dielectric substrate so as to be electrically coupled to the conductive interconnects;
wherein each of the first and second magneto-resistance sensor chips comprises at least one magneto-resistance sensor circuit, with the first and second magneto-resistance sensor chips being attached to the flex circuit such that an orientation of the at least one magneto-resistance sensor circuit on the first magneto-resistance sensor chip is different from an orientation of the at least one magneto-resistance sensor circuit on the second magneto-resistance sensor chip by a known angle; and
wherein the dielectric substrate is folded at a location between the first and second magneto-resistance sensor chips such that the flex circuit comprises a first substrate portion and a second substrate portion oriented orthogonal to one another, with the first magneto-resistance sensor chip attached to the first substrate portion and the second magneto-resistance sensor chip attached to the second substrate portion.

18. The multi-axis magneto-resistance sensor package of claim 17 further comprising a third magneto-resistance sensor chip aligned with the first magneto-resistance sensor chip along a lengthwise direction of the flex circuit, such that a width of the multi-axis magneto-resistance sensor package is approximately equal to a width of the first and third magneto-resistance sensor chips.

19. The multi-axis magneto-resistance sensor package of claim 17 wherein the first and second substrate portions oriented orthogonal to one another form an L-shaped flex circuit.

* * * * *

UNITED STATES PATENT AND TRADEMARK OFFICE
CERTIFICATE OF CORRECTION

PATENT NO. : 9,995,600 B2  
APPLICATION NO. : 14/842578  
DATED : June 12, 2018  
INVENTOR(S) : Nagarkar et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 136 days.

Signed and Sealed this
Fifth Day of March, 2019

Andrei Iancu
*Director of the United States Patent and Trademark Office*